United States Patent
Koss et al.

(10) Patent No.: US 8,764,816 B2
(45) Date of Patent: Jul. 1, 2014

(54) STENT DELIVERY AND DEPLOYMENT SYSTEM

(75) Inventors: Alexander K. Koss, Flagstaff, AZ (US); James D. Silverman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1101 days.

(21) Appl. No.: 11/745,347

(22) Filed: May 7, 2007

(65) Prior Publication Data

US 2008/0281398 A1 Nov. 13, 2008

(51) Int. Cl.
*A61F 2/06* (2013.01)

(52) U.S. Cl.
USPC .................. 623/1.23; 623/1.11; 623/1.12

(58) Field of Classification Search
USPC ....................... 623/1.12, 1.11, 1.23
See application file for complete search history.

(56) References Cited

U.S. PATENT DOCUMENTS

| | | | |
|---|---|---|---|
| 4,732,152 A | 3/1988 | Wallsten et al. | |
| 4,848,343 A | 7/1989 | Wallsten et al. | |
| 5,104,388 A | 4/1992 | Quackenbush | |
| 5,445,646 A | 8/1995 | Euteneuer et al. | |
| 5,507,767 A | 4/1996 | Maeda et al. | |
| 5,662,703 A | 9/1997 | Yurek et al. | |
| 5,993,427 A | 11/1999 | Rolland et al. | |
| 6,059,813 A | 5/2000 | Vrba et al. | |
| 6,096,027 A | 8/2000 | Layne | |
| 6,183,508 B1 | 2/2001 | Stinson et al. | |
| 6,238,410 B1 | 5/2001 | Vrba et al. | |
| 6,280,412 B1 | 8/2001 | Pederson, Jr. et al. | |
| 6,447,540 B1 * | 9/2002 | Fontaine et al. | 623/1.12 |
| 6,468,243 B1 | 10/2002 | Miyagawa | |
| 6,544,278 B1 | 4/2003 | Vrba et al. | |
| 6,607,552 B1 | 8/2003 | Hanson | |
| 6,827,731 B2 * | 12/2004 | Armstrong et al. | 623/1.12 |
| 6,942,682 B2 | 9/2005 | Vrba et al. | |
| 7,285,130 B2 | 10/2007 | Austin | |
| 2001/0044595 A1 * | 11/2001 | Reydel et al. | 604/98.02 |
| 2002/0016607 A1 | 2/2002 | Bonadio et al. | |
| 2004/0097957 A1 | 5/2004 | Jaker et al. | |
| 2005/0119719 A1 | 6/2005 | Wallace et al. | |
| 2005/0288764 A1 | 12/2005 | Snow et al. | |
| 2006/0015171 A1 | 1/2006 | Armstrong et al. | |
| 2006/0025844 A1 | 2/2006 | Majercak et al. | |

(Continued)

FOREIGN PATENT DOCUMENTS

| | | |
|---|---|---|
| WO | 00/42949 | 1/2000 |
| WO | 01/83017 | 11/2001 |
| WO | 2005/107644 | 11/2005 |

*Primary Examiner* — Victor Nguyen
*Assistant Examiner* — Kevin Everage
(74) *Attorney, Agent, or Firm* — Wayne D. House

(57) ABSTRACT

A stent delivery and deployment system for use primarily with self-expanding stents, incorporating a traction tube extending over the length of the diametrically compacted and constrained stent and everting back over itself, with the outer everted portion of the traction tube preferably extending to the proximal end of the delivery system. A constraining sleeve is provided between the inner, non-everted portion and outer, everted portion of the traction tube, the constraining sheath extending over the length of the constrained stent prior to deployment and diametrically constraining the diametrically compacted self-expanding stent. The application of tension to the proximal end of the traction tube causes the constraining sheath to move in a proximal direction, freeing the constrained stent as it moves and allowing the stent to deploy against the wall of the body conduit within which it is located during the deployment process.

9 Claims, 8 Drawing Sheets

(56) References Cited

U.S. PATENT DOCUMENTS

| 2006/0030923 | A1 | 2/2006 | Gunderson |
| 2006/0041302 | A1 | 2/2006 | Malewicz |
| 2006/0173422 | A1 | 8/2006 | Reydel et al. |
| 2006/0200221 | A1* | 9/2006 | Malewicz ................ 623/1.11 |
| 2007/0198077 | A1 | 8/2007 | Cully et al. |

* cited by examiner

STENT DELIVERY AND DEPLOYMENT SYSTEM

FIELD OF THE INVENTION

The invention relates to the field of delivery and deployment systems for implantable stents.

BACKGROUND OF THE INVENTION

The accurate delivery and deployment of expandable medical devices such as stent devices remains a significant challenge to medical practitioners. These stent devices when deployed and implanted provide support to tubular body conduits such as blood vessels or biliary ducts. Preferably, the stent delivery system including the loaded stent device offers good flexibility in bending, in order that the stent and delivery system are able to negotiate tortuous anatomy en route to the desired implantation site. Flexible stents may also be axially compressible and consequently vulnerable to inadvertent axial shortening when deployed resulting from the action of the stent delivery system during deployment. Some delivery systems impart an axially compressive force to the stent during the deployment process, which can result in undesirable axial shortening of the stent. Some stent designs are particularly vulnerable to this effect.

Expandable stent devices include stents and stent-grafts, the latter being a stent frame provided with a covering of graft material over the otherwise open interstices that exist between adjacent elements of the stent frame. Typical graft materials are flexible and usually are polymeric materials such as polyethylene terephthalate (Dacron) fabric or porous expanded polytetrafluoroethylene (ePTFE). Expandable stent devices also include vena cava filters and any other devices that may be delivered through a body conduit to a site where it is desired to implant the device. These expandable devices are typically removably affixed to a distal end of a flexible catheter that constitutes the basis of the delivery system, the catheter being the means by which the stent device is moved through the body conduit. The stent device is provided in a diametrically compacted state to enable it to be transported through the body conduit. Deployment at the desired site entails diametrical expansion of the stent device until it interferably contacts the luminal surface of the body conduit. The interference fit of the device against the wall of the body conduit results in implantation of the device at that site, either temporarily for some devices that are designed to be removable, or permanently. The diametrical expansion of the device also frees it from the distal end of the catheter-based delivery system, which is usually withdrawn from the body conduit immediately following conclusion of the deployment process.

Expandable stent devices are typically either balloon expandable or self-expanding. Both types benefit from flexible delivery systems that allow them to be routed through tortuous anatomy. In particular, self-expanding stents are vulnerable to undesirable length change as the stent is released from its constrained small introductory diameter to its full deployed diameter. An effective, flexible delivery system that minimizes deployment force and minimizes any adverse effect on the length of the stent device would be of significant benefit to practitioners and patients.

SUMMARY OF THE INVENTION

A stent delivery and deployment system is described, primarily for use with self-expanding stents. It is particularly useful for stents that are axially compliant (in the longitudinal direction, parallel to the longitudinal axis) and are vulnerable to undesirable foreshortening or lengthening during deployment, as the present system minimizes the risk of undesirable length change. Many of these axially compliant stents include flexibly connected adjacent stent elements; an example is a stent described in U.S. Pat. No. 5,507,767 to Maeda et al. Using the present system, deployment of a compacted stent from the small, compacted diameter necessary for delivery to the larger, deployed diameter substantially preserves the longitudinally oriented distance between adjacent stent elements of axially compliant stents such as stents having flexibly connected adjacent stent elements.

The present system also reduces the force required of the practitioner to cause deployment due to the use of an everted traction tube with a separate constraining sheath. This also allows for the practical, easy deployment of longer length, small diameter stents, e.g., 6 mm diameter stents of 70 mm length or greater.

For purposes of the present description, the distal end of the system is the end that the stent device is affixed to and the first portion of the system to be inserted into a patient, while the opposite proximal end is typically provided with a catheter hub and includes the necessary aspects to allow the practitioner to control the device delivery and deployment.

The system incorporates a traction tube (i.e., a tubular sheath) extending over the length of a diametrically constrained stent and everted back over itself, with the outer everted portion of the traction tube extending toward the proximal end of the delivery system. This proximal extension of the traction tube allows tension to be applied to the traction tube by a practitioner when it is desired to deploy the constrained stent. A tubular constraining sleeve (or constraining sheath) is provided between the inner portion and outer, everted portion of the traction tube for retaining the stent in its diametrically compacted state, the constraining sheath preferably extending over the length of the stent and maintaining it in a constrained state prior to deployment. The application of tension to the proximal end of the traction tube causes the constraining sheath to move in a proximal direction, freeing the constrained stent as it moves and allowing the stent to deploy against the wall of the body conduit within which it is located during the deployment process.

The constraining sheath is preferably made from a thin, relatively flexible material and is provided in a tubular form possessed of sufficient hoop strength to maintain the stent in a diametrically compacted state as necessary for transport through the length of a body conduit to the desired implant location. The tubular constraining sheath is located between the inner portion of the traction tube that coaxially surrounds the compacted stent device and is in direct contact with the device, and the outer portion of the traction tube that is everted back over the outer surface of the constraining sheath. This everted portion of the traction tube preferably extends proximally along the length of the delivery catheter shaft back to the catheter hub where it is accessible to the practitioner. When tension is applied to the proximal end of the traction tube by the practitioner, this arrangement provides an effective way to allow the constraining sheath to be moved proximally off of the compacted stent device beginning with the distal end of the device and progressing to the proximal end. The everted arrangement of the traction tube allows it to operate in similar fashion to the movement of the tracks of a tracked vehicle (e.g., a bulldozer), with the inner portion of the traction tube that surrounds the compacted stent device remaining stationary with respect to the device and consequently not imparting any axial compressive or extensive force to the device during deployment. As deployment progresses, the tension applied by the practitioner to the proximal end of the traction tube causes the inner portion of the traction tube to progressively evert over the distal end of the now-moving constraining sheath and consequently evert around to the outer surface of the constraining sheath as the stent device is progressively released in a proximal direction.

The traction tube should be comprised of a strong, thin, flexible and lubricious material. A preferred material is ePTFE. It is preferred that the inside diameter of the traction tube is larger than the inside diameter of the constraining sheath. This arrangement allows the entire diametrical force from a constrained stent device to be contained by the constraining sheath and avoids the application of hoop stress to the traction tube. The thinness and flexibility of the traction tube allows the inner portion of that everted tube to be located inside of the constraining sheath in spite of the smaller inside diameter of the constraining sheath. The smaller inside diameter of the constraining sheath ensures that the traction tube is essentially only exposed to the tensile force applied by the practitioner during deployment and as such minimizes the tensile force that is required to cause deployment.

The present system may also be used to advantage in the delivery and deployment of stent-grafts.

DETAILED DESCRIPTION OF THE DRAWINGS

Figure 1A:
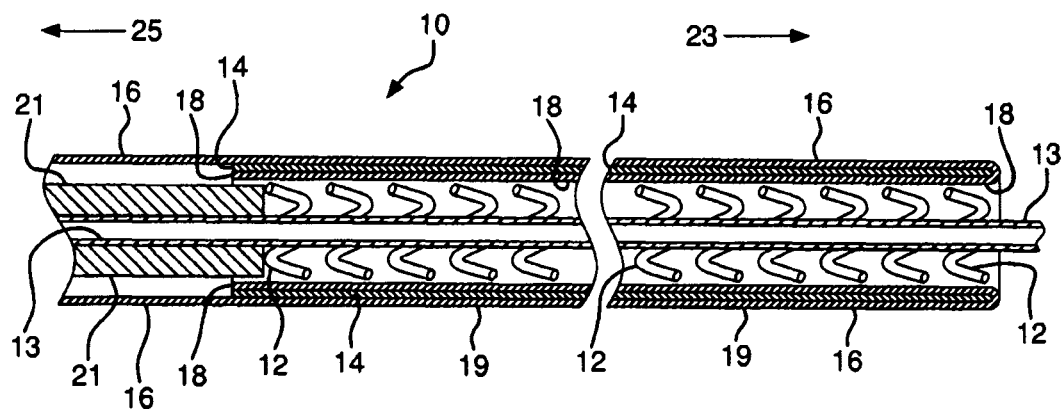
FIG. 1A is a longitudinal cross section of the distal end of the delivery system showing a compacted stent device contained within a constraining sheath that is located between an inner portion of a traction tube and an outer portion of the traction tube that is everted back over the outer surface of the constraining sheath.

FIG. 1A shows a longitudinal cross section of the distal end of the delivery and deployment system 10 describing a stent device 12 mounted on the distal end of a delivery catheter shaft 13 having a lumen that may accommodate passage of a guidewire (not shown). The distal end of system 10 is indicated by arrow 23, while the proximal end is indicated by arrow 25. Stent device 12, preferably a self-expanding stent device, is in a compacted state (prior to deployment) and is contained within a constraining sheath 14 that is located between an inner portion 18 of a traction tube 16, and an outer portion 19 of the traction tube 16 that is everted back over the outer surface of the constraining sheath 14.

Delivery catheter shaft 13 is, in this embodiment, supported exteriorly by supporting catheter shaft 21, the distal end of which abuts the proximal end of stent device 12 and provides a stop to help maintain the location of the stent device 12 at the distal end of delivery catheter shaft 13 during deployment. The combination of delivery catheter shaft 13 and supporting catheter shaft 21 provides system 10 with good 'pushability' to aid in insertion of the system through body conduits such as the vasculature. The combined delivery catheter shaft 13 and support catheter shaft 21 provide good compression resistance and column strength appropriate to enable deployment as will be further described, with appropriate flexibility to allow the combined catheter shafts to bend as necessary to follow bends in the body conduit during delivery of stent device 12 to the desired site.

Traction tube 16 is a thin-walled, lubricious tube with good axial strength properties. Constraining sheath 14 is, in comparison, a more rigid tubular structure with appropriate flexibility in bending that allows the delivery system 10 to navigate tortuous vascular systems. It has sufficient hoop strength to maintain a self-expanding stent device 12 in a compacted state for prolonged periods as necessary to meet shelf life requirements. Constraining sheath 14 has an inside diameter of dimension appropriate for the diameter of the compacted stent device 12; this inside diameter is smaller than the inside diameter of the traction tube 16 in order that the hoop stress from a compacted self-expanding stent device 12 is contained entirely by the constraining sheath 14 and not by the traction tube 16.

A recommended method of measuring the inside diameter of the flexible traction tube 16 is by gently lifting the tube over the end of a tapered mandrel provided with diameter graduations and noting the indicated diameter when the tube fits snugly about the diameter of the mandrel without forcing it further up the tapered mandrel. The tapered mandrel is a convenient method of measuring the inside diameter of the more rigid constraining sheath 14 as well. These inside diameters are determined for each of these tubular components as individual parts, separate from the assembled stent delivery and deployment system 10.

Figure 1B:
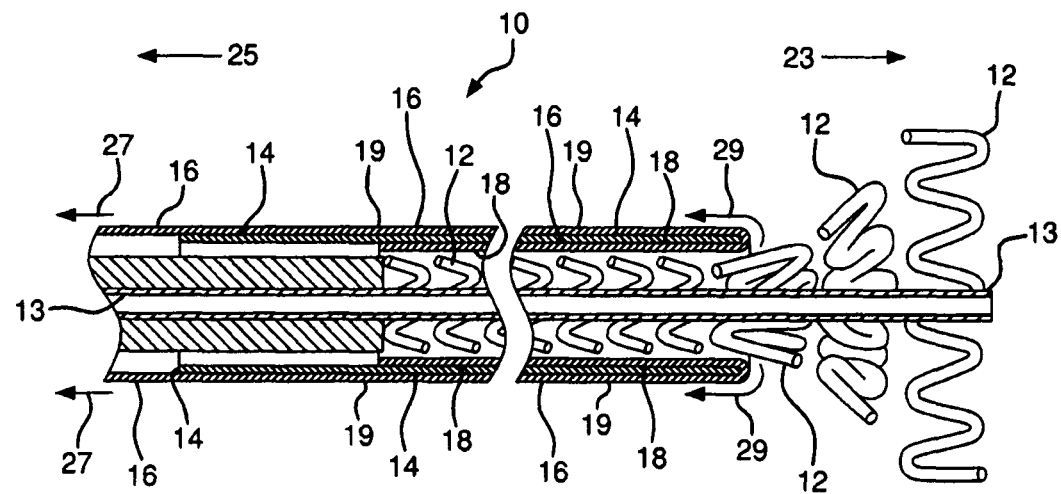
FIG. 1B is a subsequent longitudinal cross sectional view of the system of FIG. 1 showing the application of tension to the proximal end of the traction tube, resulting in progressive deployment of the stent device.

FIG. 1B is a subsequent longitudinal cross sectional view of the system of FIG. 1A showing the progressive deployment of a self-expanding stent device 12 resulting from the application of tension (indicated by arrows 27) to the proximal end of the traction tube 16. The figure illustrates how the application of tension (indicated by arrows 27) to the proximal end of traction tube 16 causes the distal end of traction tube 16 to evert (as indicated by arrows 29) around the distal end of constraining sheath 14, moving the constraining sheath 14 in a proximal direction and progressively releasing the constrained stent device 12. As the traction tube 16 everts and moves the constraining sheath 14 in a proximal direction, it is seen how the remaining, not-yet-everted inner portion 18 of the traction tube 16 that is still in contact with the remaining constrained portion of stent device 12, does not move with respect to the outer surface of stent device 12, thereby avoiding any axial imposition of force to the remaining constrained portion of stent device 12. This effect maximizes the uniform deployment of stent device 12, allowing it to contact the luminal surface of the surrounding body conduit in an accurate manner without distortion (particularly axial distortion) of the stent device 12.

The application of tension (arrow 27) to the proximal end of traction tube 16 to actuate deployment of stent device 12 is made possible by the compression resistance of delivery catheter shaft 13 and supporting catheter 21.

Figure 2A:
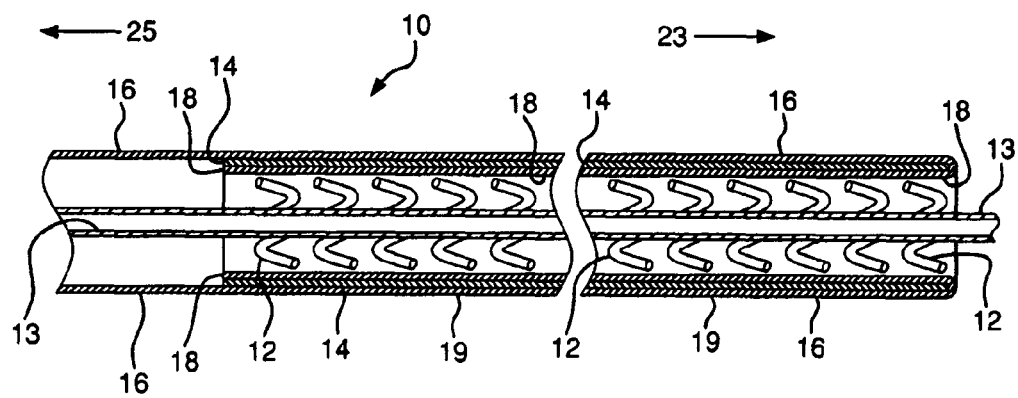
FIGS. 2A-5 are longitudinal cross sectional views showing alternative embodiments.
Figure 2B:
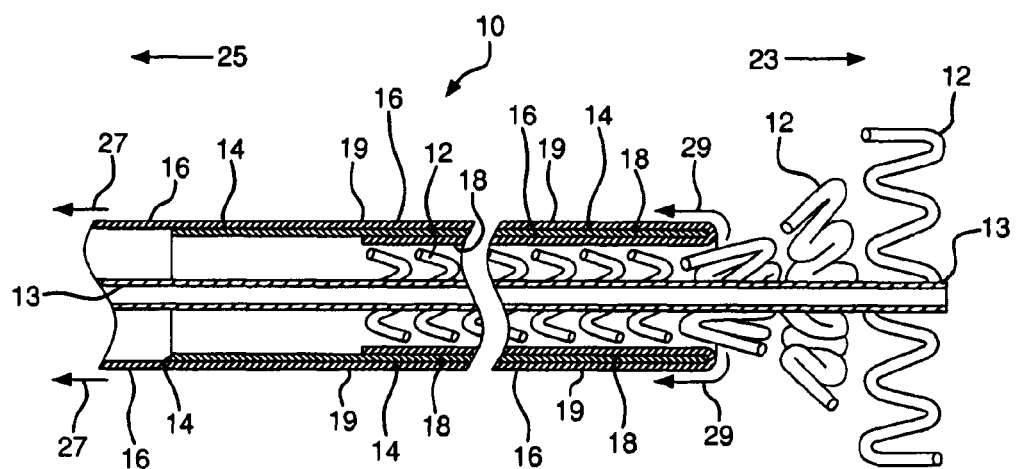

FIGS. 2A and 2B are longitudinal cross sections of alternative embodiments similar to those of FIGS. 1A and 1B, differing only in that the support catheter shaft 21 is omitted. In this embodiment, delivery catheter shaft 13 possesses the necessary physical characteristics to allow it to negotiate the vasculature during delivery of the stent device 12 to the desired site of implantation. Stent device 12 is sufficiently compacted around the outer surface of the distal end of delivery catheter shaft 13 that it is able to maintain its position on the distal end of delivery catheter shaft 13 during the deployment process.

Figure 3A:
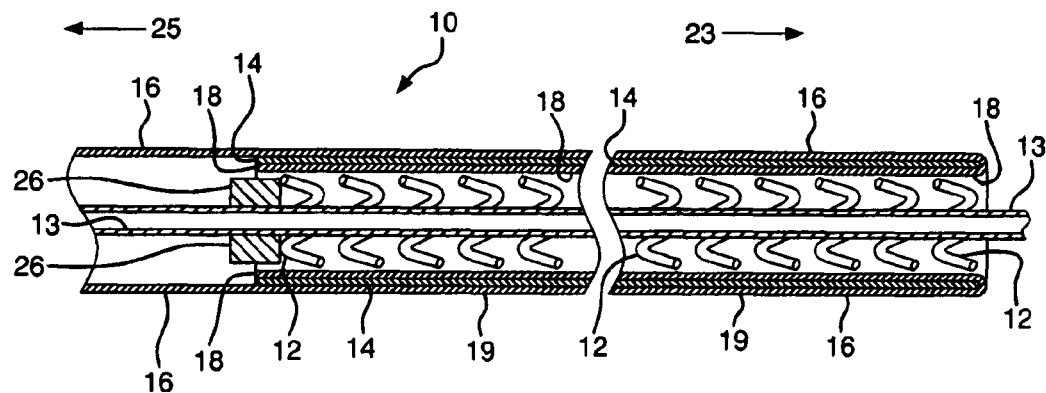
Figure 3B:
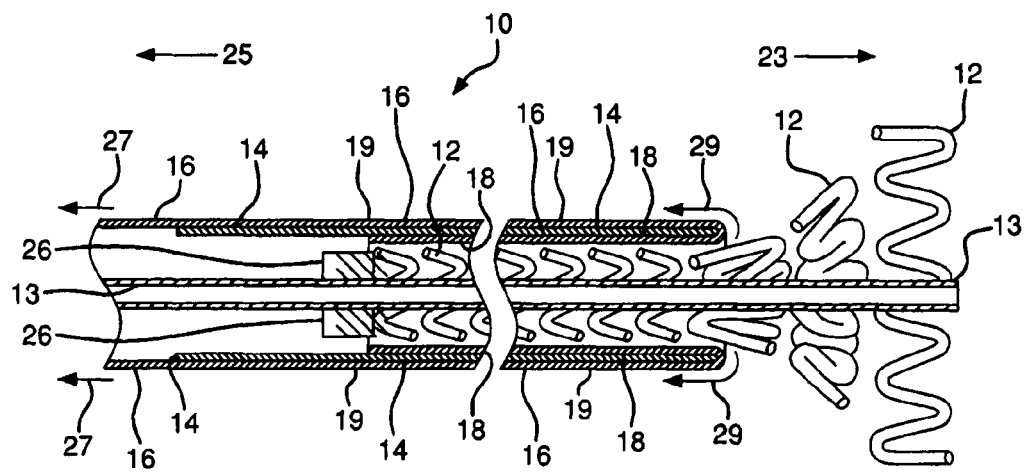

FIGS. 3A and 3B are also longitudinal cross sections of alternative embodiments similar to those of FIGS. 1A and 1B, differing only in that the support catheter shaft 21 is omitted and replaced by stop 26. Stop 26 is an annular component crimped to the outer surface of delivery catheter shaft 13 in abutting relationship to the proximal end of stent device 12, allowing stop 26 to hold the stent device 12 in position relative to the outer surface of delivery catheter shaft 13 without risk of inadvertent movement during the application of tension (arrow 27) to traction tube 16.

Figure 4:
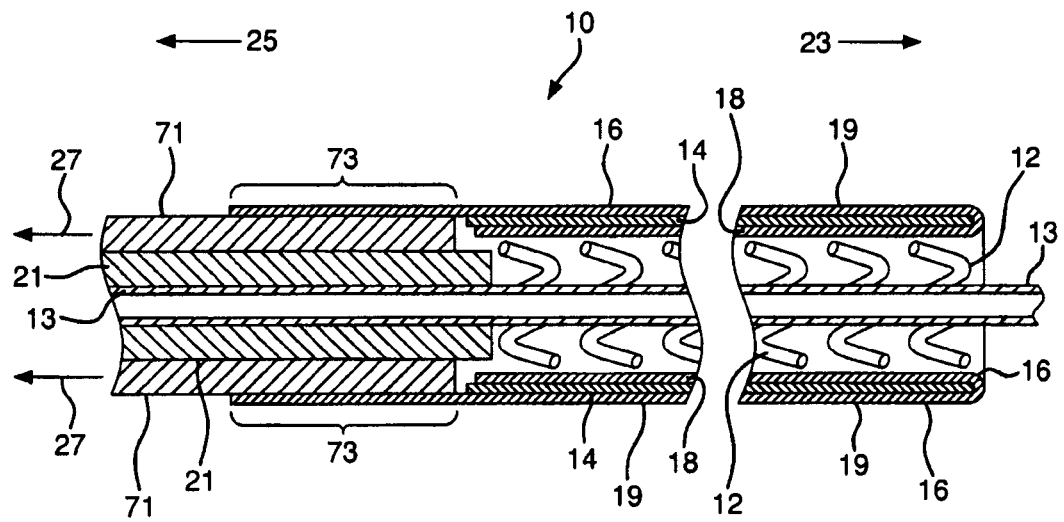

The embodiments described by FIGS. 1A-3B utilize a traction tube 16 that extends for the full length of the system 10 wherein tension (indicated by arrows 27) is applied to traction tube 16 by the practitioner at the proximal end of system 10. In another alternative described by the longitudinal cross section of FIG. 4, the traction tube 16 may extend only beyond the proximal end of stent device 12, where it is attached at region 73 (by, for example, bonding with an adhesive such as cyanoacrylate) to another catheter shaft (actuator catheter shaft 71) that is coaxial about and axially movable with respect to the outer surface of the delivery catheter shaft 13 (and supporting catheter 21 if used). This actuator catheter shaft 71 is moved proximally with respect to system 10 (as indicated by arrows 27) in order to apply tension to traction tube 16 to initiate deployment of stent device 12.

Traction tube 16 is to be made of thin, flexible, lubricious and suitably strong materials. A tube made from ePTFE is preferred. A preferred construction for the tube involves the use of ePTFE film having a predominately uniaxial microstructure. One or two layers of this film are first laid up on a mandrel of diameter and length suitable for the dimensions of the traction tube, with the high strength orientation of the film parallel to the longitudinal axis of the mandrel. A helical wrap of ePTFE tape is then wrapped around the underlying longitudinal layers, preferably with the helical wrap applied in two passes at two opposing pitch angles. In this fashion, the resulting tube is provided with good axial strength and good hoop strength. The multi-layered tube may be thermally bonded together by placing into an oven for a suitable time and temperature (e.g., in a convection oven set at 380° C. for about 8 minutes). If desired, for easier thermal bonding of the layers, the helically wrapped film may be provided with a discontinuous or continuous coating of fluorinated ethylene propylene (FEP) on the inner surface of the film as taught by U.S. Pat. No. 5,810,870.

Figure 5:
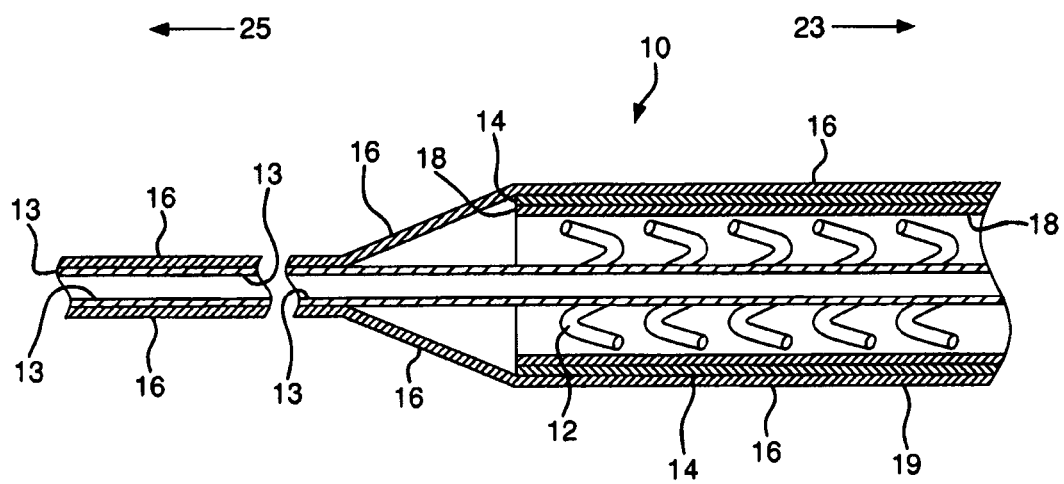

Alternatively, traction tube may be made without the longitudinally oriented ePTFE film, using only the helically wrapped film. This construction allows the traction tube to extend in length under tension, and to reduce in diameter (i.e., to "neck" under tension). The diameter reduction causes the traction tube to fit very closely around the delivery catheter shaft 13. The resulting interference fit (lack of diametrical clearance) between the inner surface of the traction tube and the outer surface of the delivery catheter shaft enhances the precision of operation and stent deployment. Preferably, a lubricant is provided between the traction tube and the delivery catheter shaft. This embodiment is described by the longitudinal cross section of FIG. 5 and may, for example, be used advantageously with embodiments generally described in FIGS. 1A-3B.

The constraining sheath may be of various polymeric materials with polyimide preferred. Likewise, the catheter shaft(s) may be any material with suitable mechanical characteristics, with some preference for polyimide/braid/Pebax® composites.

Figure 6A:
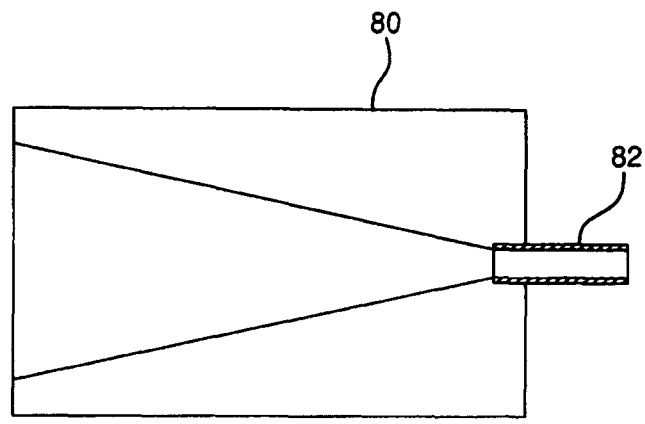
FIG. 6A is a longitudinal cross section showing a first funnel device for compacting and loading a stent into the traction tube.

The stent delivery and deployment system 10 is made by first compacting and loading a stent 12 into the traction tube 16. FIG. 6A shows a longitudinal cross section of a funnel device 80. The funnel is made with about a 15° taper and may be made of various materials including metals and plastics. Delrin® is a preferred plastic. A loading sleeve 82 is fitted into the small diameter end of funnel 80, with the inside diameter of the loading sleeve 82 matching the smallest inside diameter of funnel 80. The loading sleeve 82 should be of metal tubing (e.g., stainless steel) having a minimal wall thickness.

Figure 6B:
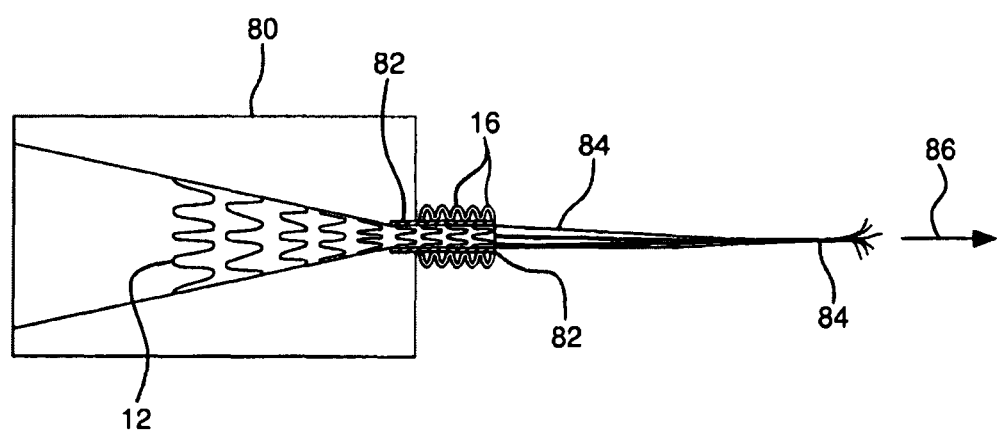
FIGS. 6B and 6C are longitudinal cross sectional views showing a stent being compacted and loaded into a traction tube using the first funnel of FIG. 6A.

FIG. 6B shows a longitudinal cross section of funnel 80 in use compacting a stent 12 to allow stent 12 to be fitted into traction tube 16. Traction tube 16 is fitted over the outer surface of loading tube 82, with the entire length of traction tube axially compressed ("scrunched") onto the outer surface of the relatively short loading tube 82. The axially compressed traction tube 16 assumes a corrugated appearance as a result of the axial compression. Stent 12 is pulled into funnel 80 by the application of tension (indicated by arrow 86) to loading fibers 84 which are temporarily attached (tied) to one end of stent 12. As stent 12 progresses from the large diameter end of funnel 80 toward the small diameter end, it is diametrically compacted as shown. Continued application of tension to loading fibers 84 pulls the small end of stent 12 through the loading tube 82.

While the use of a funnel device is described for stent compaction, there are alternative methods of compacting stents. For example, iris-type stent compacting machines are available; one type is shown in U.S. Pat. No. 6,629,350.

Figure 6C:
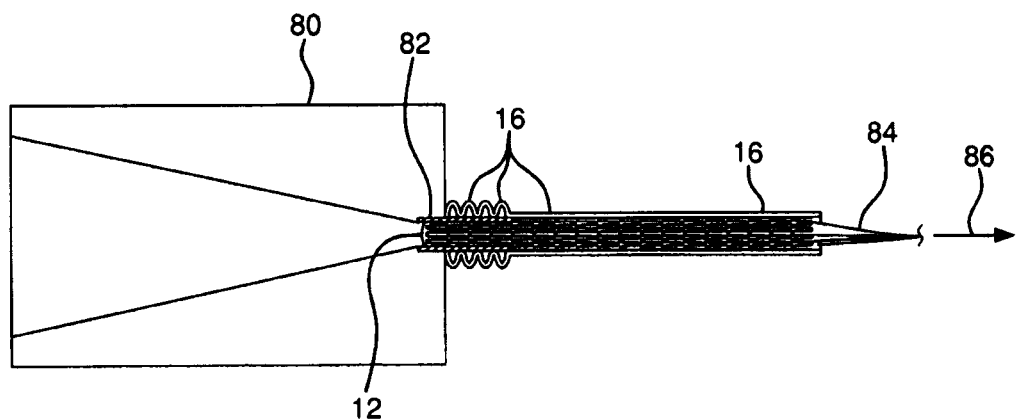

As the compacted stent 12 begins to exit the end of loading tube 82 opposite funnel 80, the corresponding end of axially compressed traction tube 16 is pushed off of the end of loading tube 82 coaxially onto the outer surface of compacted stent 12. Continued application of tension and continued progression of compacted stent 12 out of the end of loading tube 82 while traction tube 16 is simultaneously fed onto the outer surface of compacted stent 12 results in the compacted stent 12 being captured coaxially within traction tube 16 as shown by the longitudinal cross section of FIG. 6C.

Figure 7:
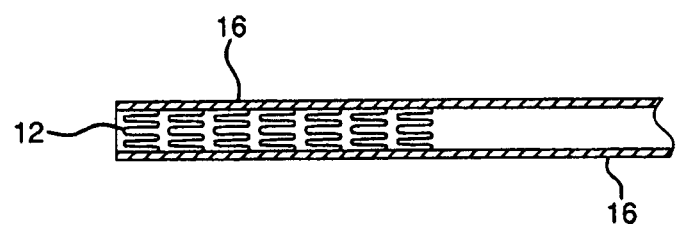
FIG. 7 shows a longitudinal cross section of a stent after being compacted and loaded into a traction tube.

FIG. 7 shows a longitudinal cross section of compacted stent 12 captured within one end of traction tube 16, with the other end of traction tube 16 extending beyond the compacted stent 12. Loading fibers 84 have been removed from the end of compacted stent 12 to which they were previously attached, i.e., the end of compacted stent 12 that is adjacent to the end of traction tube 16.

Figure 8A:
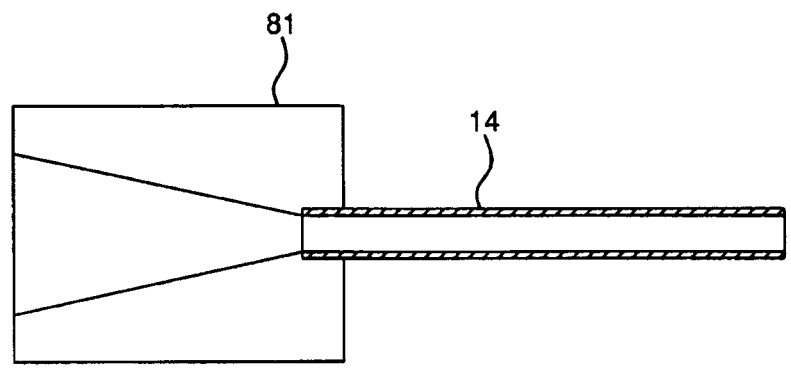
FIG. 8A is a longitudinal cross section of a constraining sheath fitted to a second funnel device prior to loading of the stent and traction tube assembly.

A second funnel 81, shown in the longitudinal cross section of FIG. 8A, is used to assemble the compacted stent 12 and traction tube 16 (as shown in FIG. 7) into constraining sheath 14. The constraining sheath 14 of length appropriate for stent 12 is temporarily fitted into a bore at the small diameter end of funnel 81. The inside diameter of constraining sheath 14 corresponds with the smallest diameter of funnel 81 and is aligned with that diameter as shown by FIG. 8A. This inside diameter is somewhat smaller that the smallest inside diameter of the first funnel 80 used to initially compact stent 12 for capture within traction tube 16. Again, the inside diameter of constraining sheath 14 is smaller than the inside diameter of traction tube 16.

Figure 8B:
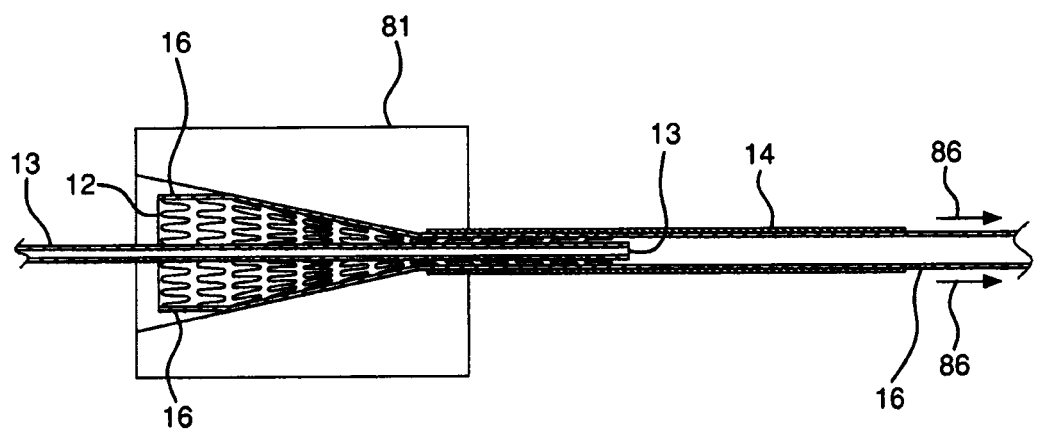
FIG. 8B is a longitudinal cross section showing the stent and traction tube assembly of FIG. 7 being further compacted and loaded into the constraining sheath, along with a delivery catheter shaft, via the second funnel.

As shown by the longitudinal cross section of FIG. 8B, the extended end of traction tube 16 that is opposite the end containing stent 12 is inserted into the large diameter end of funnel 81 and on through the small diameter end and through the constraining sheath 14 until it emerges from the opposite end of constraining sheath 14. A length of catheter shaft 13 is inserted through stent 12 and traction tube 16 until it reaches slightly beyond the end of stent 12. Tension is applied to the emerged end of traction tube 16 (as indicated by arrows 86), thereby pulling stent 12 and the opposite end of traction tube 16 into constraining sheath 14, while maintaining the positional relationship of the ends of delivery catheter shaft 13 and stent 12. The progression of this process further compacts stent 12 onto the outer surface of delivery catheter shaft 13 while introducing stent 12 and traction tube 16 into constraining sheath 14, as shown in FIG. 8B.

Figure 9A:
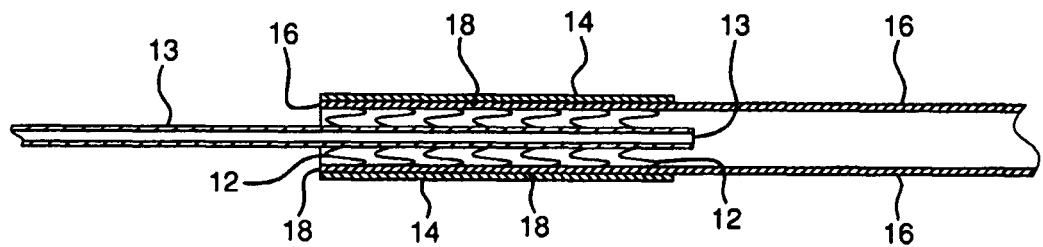
FIG. 9A shows a longitudinal cross section of the stent after compaction onto the delivery catheter shaft and after having been loaded into the traction tube and constraining sheath.
Figure 9B:
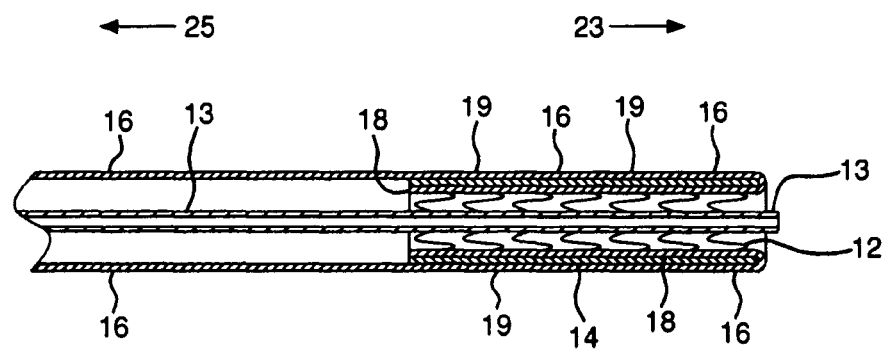
FIG. 9B shows a longitudinal cross section of the traction tube after the proximal end of the traction tube has been everted back over the outer surface of the constraining sheath.

FIG. 9A is a longitudinal cross section that shows the result of the completed loading process involving the second funnel 81. Stent 12 is compacted onto the outer surface of one end of delivery catheter shaft 13, and compacted stent 12 with traction tube 16 are captured coaxially within constraining sheath 14. Finally, the free end of traction tube 16 is everted over the outer surface of constraining sheath 14, appearing as shown in the longitudinal cross section of FIG. 9B following conclusion of the full eversion of the free length of traction tube 16.

EXAMPLE

A traction tube was formed from a thin film thickness (less than 0.025 mm) of ePTFE. The film had a bulk density of approximately 0.5 grams/cc and an approximate fibril length of about 50 microns, and had been expanded along its length with the predominant strength direction falling parallel to the length of the film. Three layers of this film were wrapped around a stainless steel mandrel having a diameter of 3 mm, with the length of the film parallel to the longitudinal axis of the mandrel. Another length of this film was provided with a discontinuous coating of FEP as taught by U.S. Pat. No. 5,810,870, and then cut to a narrow width to create a tape about 12.5 mm wide. A length of this tape was helically wrapped around the mandrel provided with the previously applied longitudinally oriented film layers, with each successive wrap overlapping half of the width of the previous wrap. The FEP coating faced the surface of the mandrel. A second helical wrap was applied in the same manner starting at the opposite end of the mandrel from the beginning of the first helical wrap. The mandrel and film were then heated in a convection oven set at 380° C. for approximately 8 minutes to bond the film layers together, after which the film tube was stripped from the mandrel. The resulting traction tube was about 2.5 times the length of the stent that was intended to be subsequently loaded.

The constraining sheath was a commercially available tube (MicroLumen Inc., Tampa Fla. 33614, part no. Sheath 0.0735×0.0795) having an inside diameter of 1.88 mm and an outside diameter of 2.01 mm. The tube was constructed with an inner liner of polyimide, stainless steel wire braid reinforcement and a polyether block amide outer layer.

The delivery catheter shaft was a length of commercially available catheter tubing (High Performance Conductors, Inc, product identity 0.0220" Polyimide/Braid/Pebax® 55D Tubes, 0.0030 inch wall, M.G., Inman S.C. 29349) having an inside diameter of 0.56 mm and an outside diameter of 0.71 mm. The tube is constructed with an inner liner of polyimide, stainless steel wire braid reinforcement and a polyether block amide outer layer.

Loading of a Cordis S.M.A.R.T.® Stent (6 mm deployed diameter, 80 mm length; Cordis Corp., Miami Lakes Fla. 33014) was accomplished with a loading funnel as described above. After loading the stent into the traction tube, the tube extended beyond the stent approximately 1.5 times the stent length on one end and 2 cm on the other. A length of the delivery catheter shaft tubing was inserted into the lumen of the partially compressed stent. The traction tube was threaded through a second funnel and through the constraining sheath, also as described above. Tension was then applied to the traction-tube to pull the stent into the constraining sheath. The traction tube was then everted over the constraining sheath. The proximal end of the distal shaft and traction tube were bonded to a compressively rigid catheter component (a polyimide tube with braided stainless steel wire reinforcement (0.79 mm inside diameter and 1.09 mm outside diameter) with a cyanoacrylate adhesive. The everted portion of the traction tube was similarly bonded to a second, translatable catheter component (inside diameter 1.32 mm and outside diameter 1.51 mm, MicroLumen Inc., Tampa Fla. 33614, part no. 520-III 75) positioned coaxial to the first. Deployment of the stent was accomplished by applying opposing forces to the two catheter components, which then tensioned the traction tube, smoothly retracting the constraining sheath and deploying the stent.

While the principles of the invention have been made clear in the illustrative embodiments set forth herein, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

We claim:

1. A deployment system for a self-expanding stent, comprising, prior to initiating deployment of the self-expanding stent, a self-expanding stent having a length extending between proximal and distal ends and having a smaller compacted diameter prior to deployment and a larger deployed diameter;
   a first tubular sheath having a first length portion that coaxially surrounds at least a substantial portion of the length of said compacted stent; and
   a second tubular sheath that coaxially surrounds the first length portion of the first tubular sheath and the substantial portion of the length of the compacted stent; and
   a second length portion of the first tubular sheath that everts back over and coaxially surrounds: the second tubular sheath, the first length portion of the first tubular sheath and at least the substantial portion of the length of the compacted stent;
   wherein the application of tension from a proximal direction to a proximal end of the second length portion of the first tubular sheath causes the first length portion of the first tubular sheath to progressively evert over the distal end of the second tubular sheath as the second tubular sheath moves in a proximal direction, thereby deploying the stent to the larger diameter beginning at the distal end of the stent.

2. A deployment system according to claim 1 wherein deployment is initiated by application of tension to one end of the first tubular sheath.

3. A deployment system according to claim 1 wherein deployment of the stent results from the application of tension to the second length portion of the first tubular sheath.

4. A deployment system according to claim 1 wherein said first tubular sheath comprises porous expanded polytetrafluoroethylene.

5. A deployment system according to claim 4 wherein said second tubular sheath comprises polyimide.

6. A deployment system according to claim 1 wherein said second tubular sheath comprises polyimide.

7. A deployment system according to claim 1 wherein said stent is compacted onto a portion of an outer surface of a catheter shaft.

8. A deployment system according to claim 1 wherein said stent has flexibly connected adjacent stent elements.

9. A deployment system according to claim 1 wherein said second tubular sheath has a smaller inside diameter than said first tubular sheath.

* * * * *